United States Patent
Barrelle et al.

(10) Patent No.: US 10,532,005 B2
(45) Date of Patent: Jan. 14, 2020

(54) ADAPTOR FOR COUPLING TO A MEDICAL CONTAINER

(71) Applicant: Becton Dickinson Holdings Pte. Ltd., Singapore (SG)

(72) Inventors: Laurent Barrelle, Saint Nizier du Moucherotte (FR); Anthony C. J. Fernando, Singapore (SG)

(73) Assignee: Becton Dickinson Holdings Pte. Ltd., Singapore (SG)

( * ) Notice: Subject to any disclaimer, the term of this patent is extended or adjusted under 35 U.S.C. 154(b) by 201 days.

(21) Appl. No.: 15/374,032

(22) Filed: Dec. 9, 2016

(65) Prior Publication Data

US 2017/0087057 A1 Mar. 30, 2017

Related U.S. Application Data

(63) Continuation of application No. 14/375,196, filed as application No. PCT/SG2013/000043 on Feb. 1, 2013, now Pat. No. 9,549,873.

(30) Foreign Application Priority Data

Feb. 2, 2012 (SG) .................................. 201200772

(51) Int. Cl.
*A61J 1/14* (2006.01)
*A61J 1/20* (2006.01)
(Continued)

(52) U.S. Cl.
CPC ............. *A61J 1/1406* (2013.01); *A61J 1/035* (2013.01); *A61J 1/201* (2015.05); *A61J 1/2055* (2015.05);
(Continued)

(58) Field of Classification Search
CPC ........ A61J 1/1406; A61J 1/201; A61J 1/2082; A61J 1/2055; A61J 1/2096; A61J 1/035;
(Continued)

(56) References Cited

U.S. PATENT DOCUMENTS 3,940,003 A 2/1976 Larson
4,564,045 A 1/1986 Koch et al.
(Continued)

FOREIGN PATENT DOCUMENTS

CN 1901955 A 1/2007
CN 101686896 A 3/2010
(Continued)

*Primary Examiner* — Nicolas A Arnett
(74) *Attorney, Agent, or Firm* — The Webb Law Firm

(57) ABSTRACT

An adaptor for coupling with a medical container, including: a tubular body receiving a pierceable elastomeric piece, defining an inner cavity of the adaptor, the pierceable elastomeric piece being movable within the tubular body between a first position, in which a distal part of the pierceable elastomeric piece forms a seal of the cavity, and a second position, proximally spaced from the first position, in which the distal part opens the seal of the cavity, an air inlet, a filtering system for filling the inner cavity with decontaminated air, and a gripping member for securing the adaptor to the medical container. Also, an assembly comprising such an adaptor and a medical container.

10 Claims, 10 Drawing Sheets

(51) Int. Cl.
*A61J 1/03* (2006.01)
*A61L 2/00* (2006.01)
*B65B 3/00* (2006.01)

(52) U.S. Cl.
CPC ........... *A61J 1/2082* (2015.05); *A61J 1/2096* (2013.01); *A61L 2/0082* (2013.01); *A61L 2/0088* (2013.01); *B65B 3/003* (2013.01); *A61J 1/2075* (2015.05); *A61L 2202/23* (2013.01)

(58) Field of Classification Search
CPC ...... A61J 1/2075; B65B 3/003; A61L 2/0082; A61L 2/0088; A61L 2202/23
See application file for complete search history.

(56) References Cited

U.S. PATENT DOCUMENTS

| | | | |
|---|---|---|---|
| 4,576,211 A | 3/1986 | Valentini et al. | |
| 4,619,651 A * | 10/1986 | Kopfer | A61J 1/2096 604/414 |
| 4,768,568 A | 9/1988 | Fournier et al. | |
| 5,342,319 A | 8/1994 | Watson et al. | |
| 5,454,409 A | 10/1995 | McAffer et al. | |
| 5,498,253 A | 3/1996 | Aswad et al. | |
| 5,529,189 A * | 6/1996 | Feldschuh | A61M 5/31511 206/365 |
| 5,533,994 A | 7/1996 | Meyer | |
| 5,620,433 A | 4/1997 | Aswad et al. | |
| 5,678,718 A | 10/1997 | Morris et al. | |
| 5,769,825 A * | 6/1998 | Lynn | A61M 5/002 604/191 |
| 5,772,652 A | 6/1998 | Zielinski | |
| 5,827,262 A | 10/1998 | Neftel et al. | |
| 5,829,589 A | 11/1998 | Nguyen et al. | |
| 5,887,633 A | 3/1999 | Yale et al. | |
| 5,931,828 A * | 8/1999 | Durkee | B65D 51/002 215/247 |
| 5,997,811 A * | 12/1999 | Esposito | A61B 10/0096 422/1 |
| 6,022,339 A * | 2/2000 | Fowles | A61J 1/10 604/411 |
| 6,258,078 B1 | 7/2001 | Thilly | |
| 6,261,282 B1 | 7/2001 | Jepson et al. | |
| 6,280,430 B1 | 8/2001 | Neftel et al. | |
| 6,341,802 B1 | 1/2002 | Matkovich | |
| 6,358,236 B1 * | 3/2002 | DeFoggi | A61J 1/2096 604/403 |
| 6,379,340 B1 * | 4/2002 | Zinger | A61J 1/2089 604/246 |
| 6,453,956 B2 | 9/2002 | Safabash | |
| 6,527,738 B1 * | 3/2003 | Jones | A61M 5/1409 604/84 |
| 6,571,837 B2 | 6/2003 | Jansen et al. | |
| 6,582,415 B1 * | 6/2003 | Fowles | A61J 1/1406 137/614.04 |
| 6,626,309 B1 | 9/2003 | Jansen et al. | |
| 6,655,655 B1 | 12/2003 | Matkovich et al. | |
| 6,715,520 B2 | 4/2004 | Andreasson et al. | |
| 6,729,370 B2 | 5/2004 | Norton et al. | |
| 6,802,828 B2 * | 10/2004 | Reynolds | A61J 1/062 604/199 |
| 6,880,722 B2 | 4/2005 | Anderson et al. | |
| 7,100,646 B2 | 9/2006 | Py et al. | |
| 7,263,411 B2 | 8/2007 | Shows et al. | |
| 7,354,427 B2 | 4/2008 | Fangrow | |
| 7,382,692 B1 | 6/2008 | Hildebrandt | |
| 7,530,974 B2 | 5/2009 | Domkowski et al. | |
| 7,621,273 B2 | 11/2009 | Morton et al. | |
| 7,708,719 B2 * | 5/2010 | Wilmot | A61J 1/062 206/364 |
| 7,731,678 B2 * | 6/2010 | Tennican | A61J 1/2096 604/88 |
| 7,743,799 B2 | 6/2010 | Mosler et al. | |
| 7,753,891 B2 * | 7/2010 | Tennican | A61J 1/2096 604/205 |
| 7,805,216 B2 | 9/2010 | Shows et al. | |
| 8,002,130 B2 | 8/2011 | Thilly | |
| 8,002,737 B2 * | 8/2011 | Tennican | A61J 1/2096 604/89 |
| 8,021,325 B2 * | 9/2011 | Zinger | A61J 1/2096 604/89 |
| 8,034,042 B2 | 10/2011 | Domkowski et al. | |
| 8,042,714 B2 | 10/2011 | Miyazaki et al. | |
| 8,090,471 B2 | 1/2012 | Shows et al. | |
| 8,091,727 B2 | 1/2012 | Domkowski | |
| 8,113,199 B2 | 2/2012 | Augustyn et al. | |
| 8,122,923 B2 | 2/2012 | Kraus et al. | |
| 8,123,736 B2 | 2/2012 | Kraushaar et al. | |
| 8,157,784 B2 | 4/2012 | Rogers | |
| 8,196,614 B2 | 6/2012 | Kriheli | |
| 8,225,949 B2 | 7/2012 | Aneas | |
| 8,303,572 B2 | 11/2012 | Adair et al. | |
| 8,479,732 B2 | 7/2013 | Stuart et al. | |
| 8,523,838 B2 | 9/2013 | Tornqvist | |
| 8,752,598 B2 * | 6/2014 | Denenburg | A61J 1/2089 141/105 |
| 9,333,288 B2 * | 5/2016 | Hilliard | A61M 5/002 |
| 9,522,097 B2 * | 12/2016 | Tennican | A61M 5/002 |
| 9,597,260 B2 * | 3/2017 | Ivosevic | A61J 1/2096 |
| 10,046,156 B2 * | 8/2018 | Gardner | A61M 39/16 |
| 2004/0119203 A1 | 6/2004 | Keirstead et al. | |
| 2004/0199139 A1 | 10/2004 | Fowles et al. | |
| 2009/0050213 A1 | 2/2009 | Biddell et al. | |
| 2009/0120934 A1 | 5/2009 | Domkowski | |
| 2009/0194453 A1 * | 8/2009 | Thorne, Jr. | A61J 1/2096 206/571 |
| 2009/0314291 A1 | 12/2009 | Anderson et al. | |
| 2010/0049144 A1 | 2/2010 | McConnell et al. | |
| 2010/0059474 A1 | 3/2010 | Brandenburger et al. | |
| 2010/0137827 A1 | 6/2010 | Warren et al. | |
| 2010/0176080 A1 | 7/2010 | Grunert et al. | |
| 2010/0241088 A1 | 9/2010 | Ranalletta et al. | |
| 2011/0147333 A1 | 6/2011 | Grek et al. | |
| 2012/0000569 A1 | 1/2012 | Wiegel | |
| 2012/0012631 A1 * | 1/2012 | Thorne, Jr. | A61J 1/16 225/1 |
| 2012/0116579 A1 | 5/2012 | Shows et al. | |
| 2012/0123381 A1 | 5/2012 | Kraus et al. | |
| 2012/0203193 A1 | 8/2012 | Rogers | |
| 2013/0204201 A1 | 8/2013 | Avery et al. | |
| 2013/0231630 A1 | 9/2013 | Kraus et al. | |
| 2013/0253432 A1 | 9/2013 | Avery et al. | |
| 2013/0345626 A1 * | 12/2013 | Tennican | A61M 5/002 604/89 |
| 2014/0163468 A1 | 6/2014 | Avery et al. | |

FOREIGN PATENT DOCUMENTS

| | | |
|---|---|---|
| EP | 0696994 B1 | 12/1996 |
| EP | 0836465 A1 | 4/1998 |
| EP | 0904763 A2 | 3/1999 |
| EP | 0960616 A2 | 12/1999 |
| EP | 1034772 A1 | 9/2000 |
| EP | 1221924 B1 | 3/2004 |
| EP | 1539577 A2 | 6/2005 |
| EP | 1687203 A2 | 8/2006 |
| EP | 1962932 A2 | 9/2008 |
| EP | 1879642 B1 | 7/2009 |
| EP | 2114345 A1 | 11/2009 |
| EP | 2298406 A1 | 3/2011 |
| EP | 2383199 A1 | 11/2011 |
| EP | 2555814 A1 | 2/2013 |
| EP | 2555815 A1 | 2/2013 |
| EP | 2560049 A2 | 2/2013 |
| EP | 2603260 A1 | 6/2013 |
| EP | 1730676 B1 | 8/2013 |
| FR | 2560049 A1 | 8/1985 |
| FR | 2708204 A1 | 2/1995 |
| WO | 9400094 A1 | 1/1994 |
| WO | 9507066 A1 | 3/1995 |

(56) References Cited

FOREIGN PATENT DOCUMENTS

| WO | 0152920 A2 | 7/2001 |
|---|---|---|
| WO | 2004073775 A1 | 9/2004 |
| WO | 2011072226 A1 | 6/2011 |
| WO | 2012118923 A2 | 9/2012 |

* cited by examiner

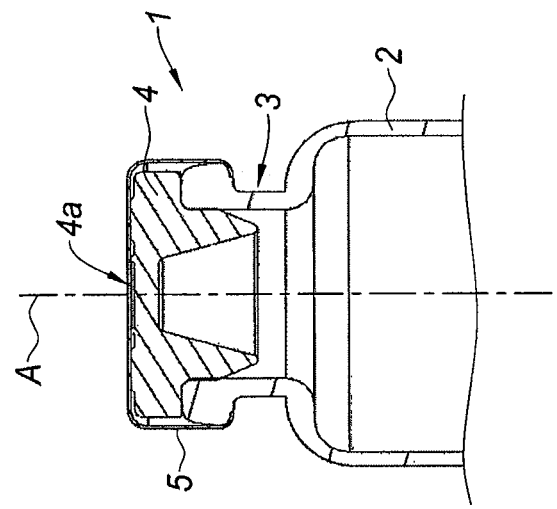
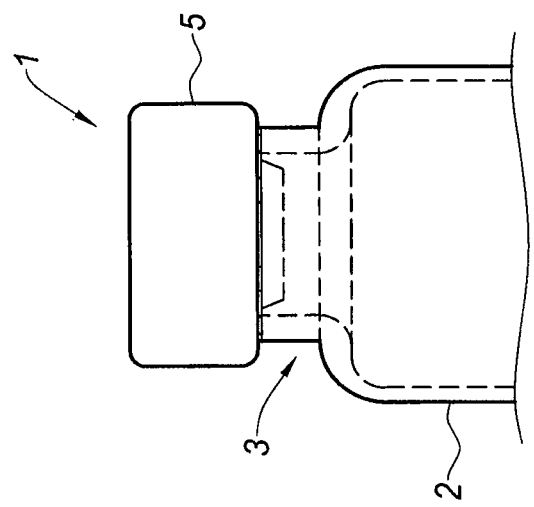
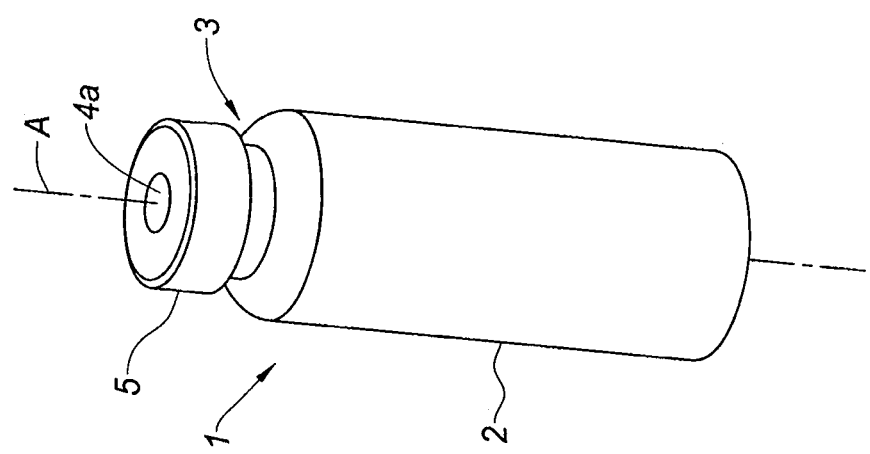

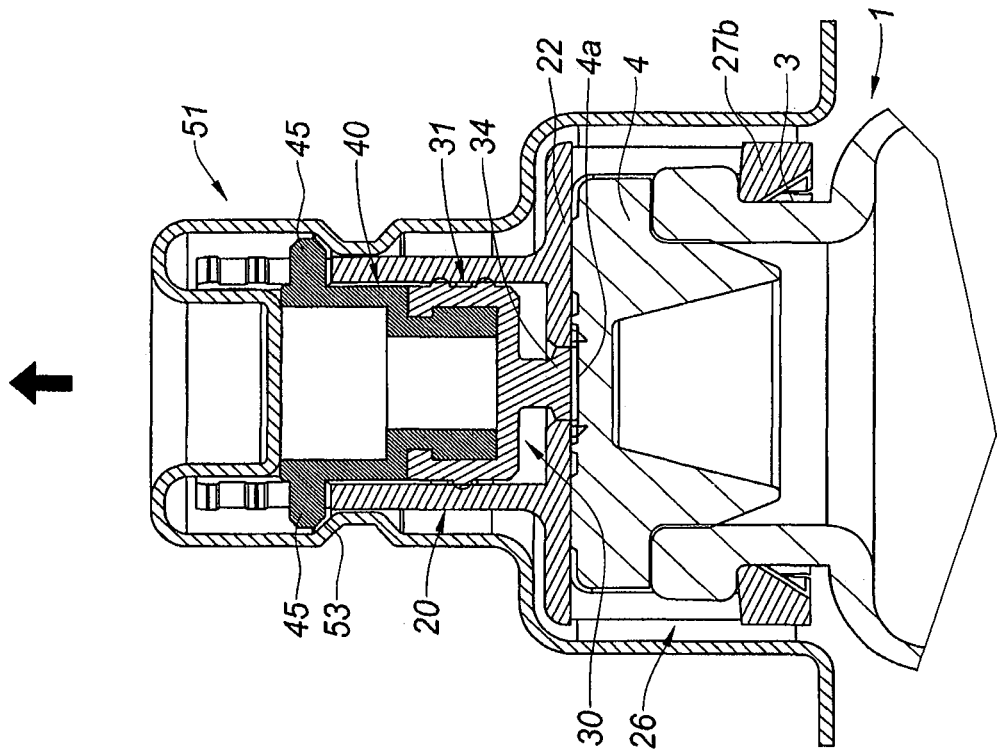
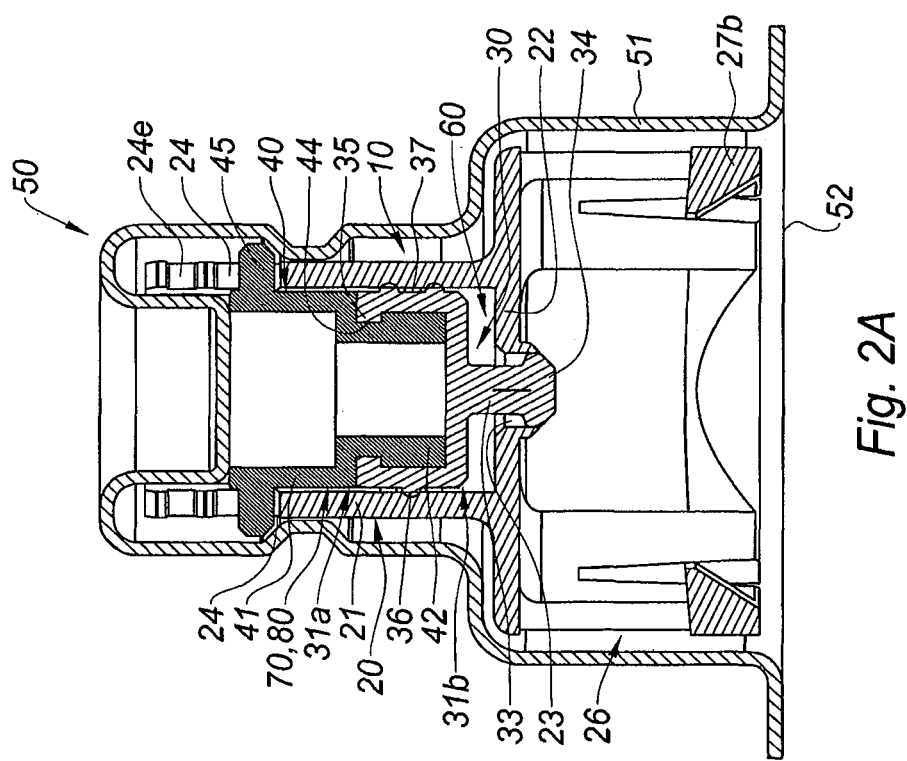
Fig. 2A
Fig. 2B

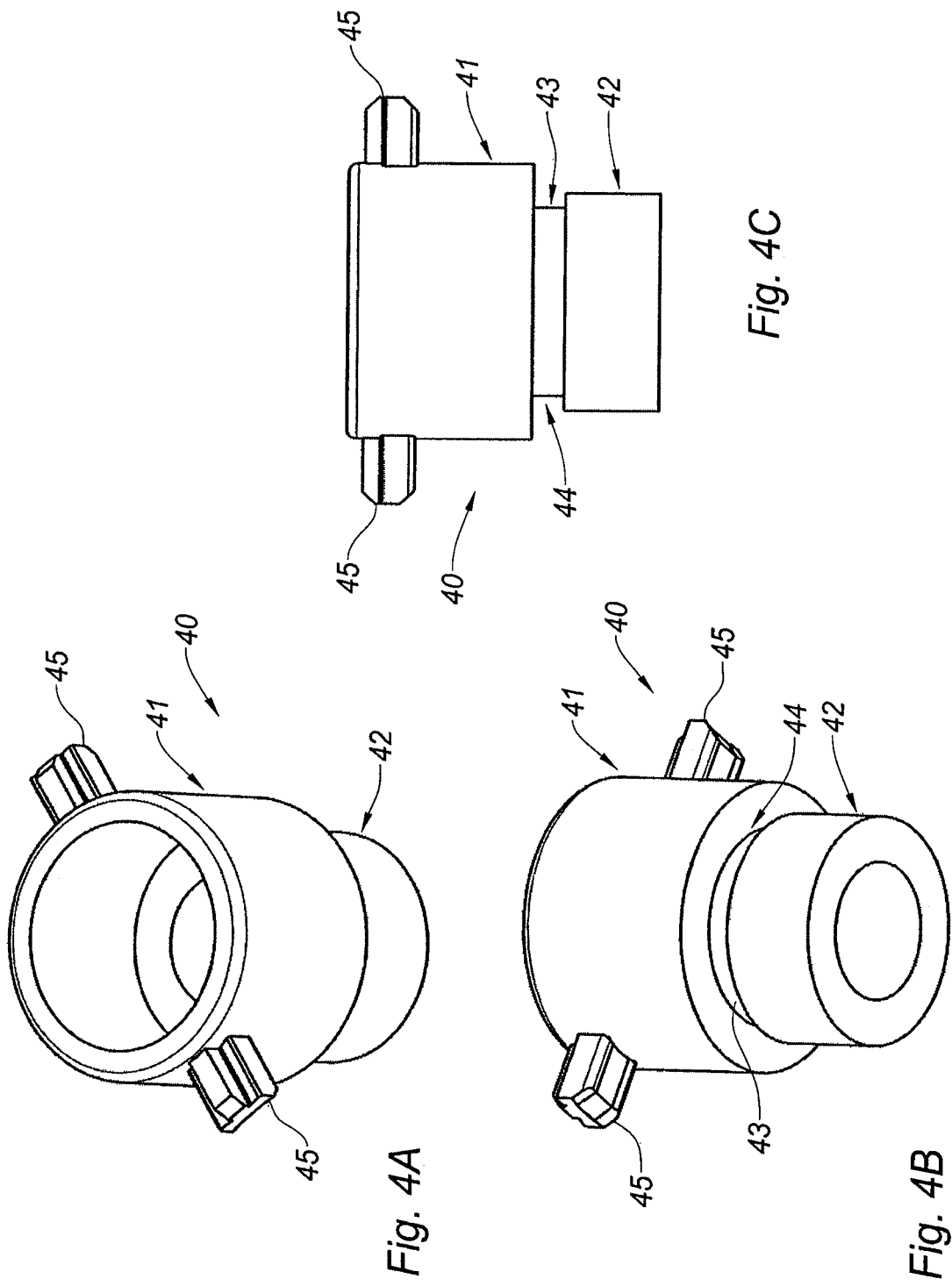

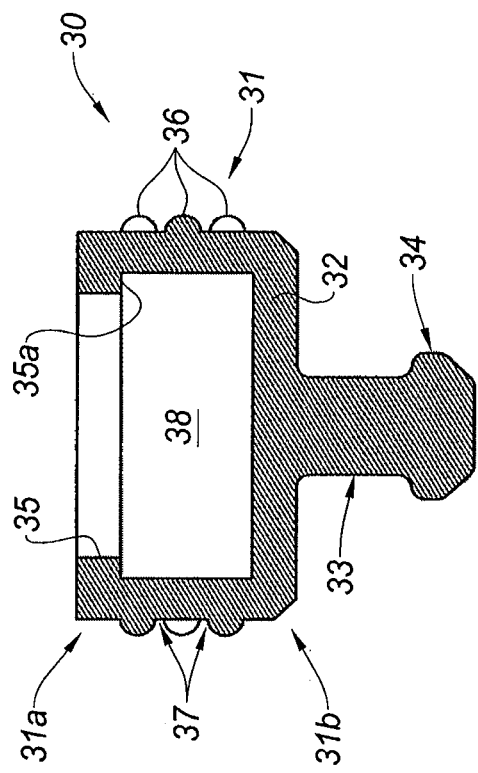
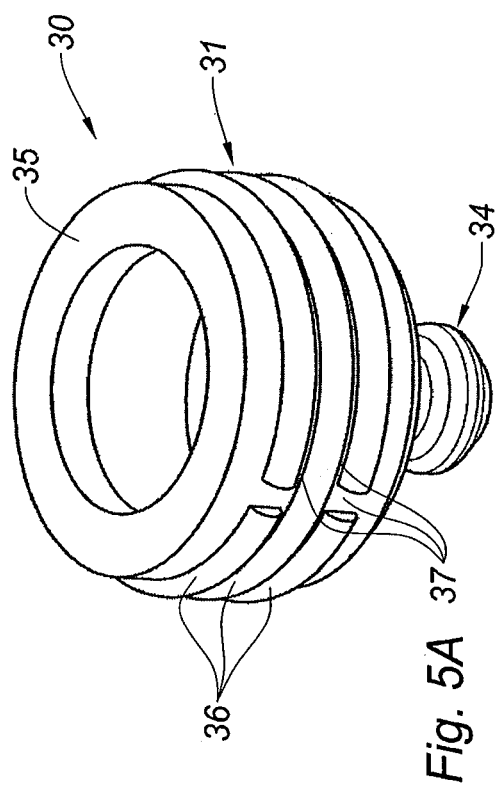
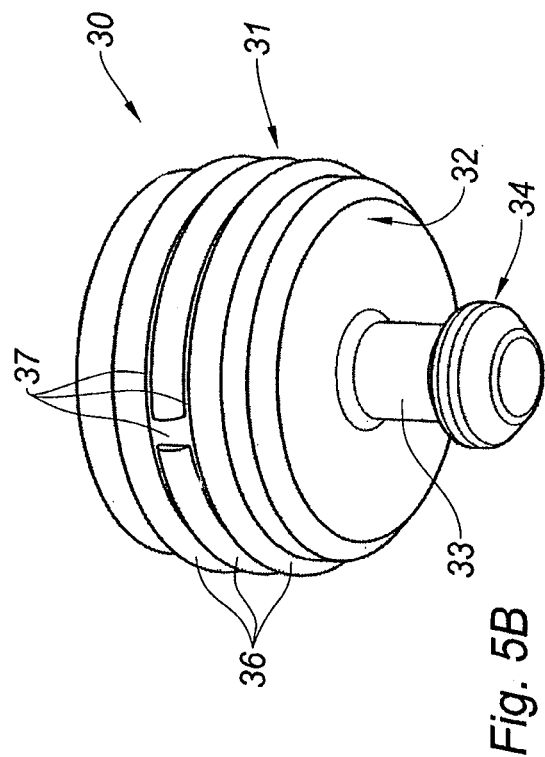

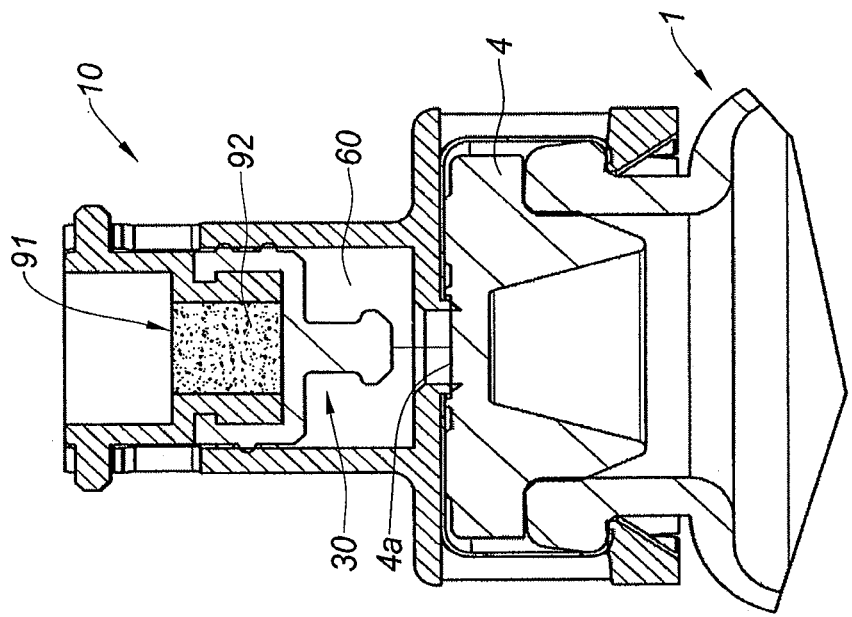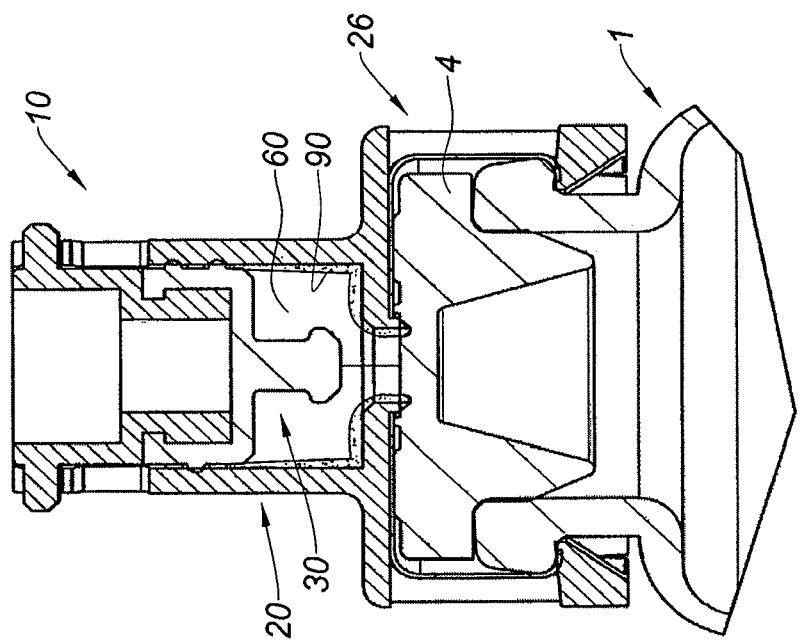
Fig. 7
Fig. 8

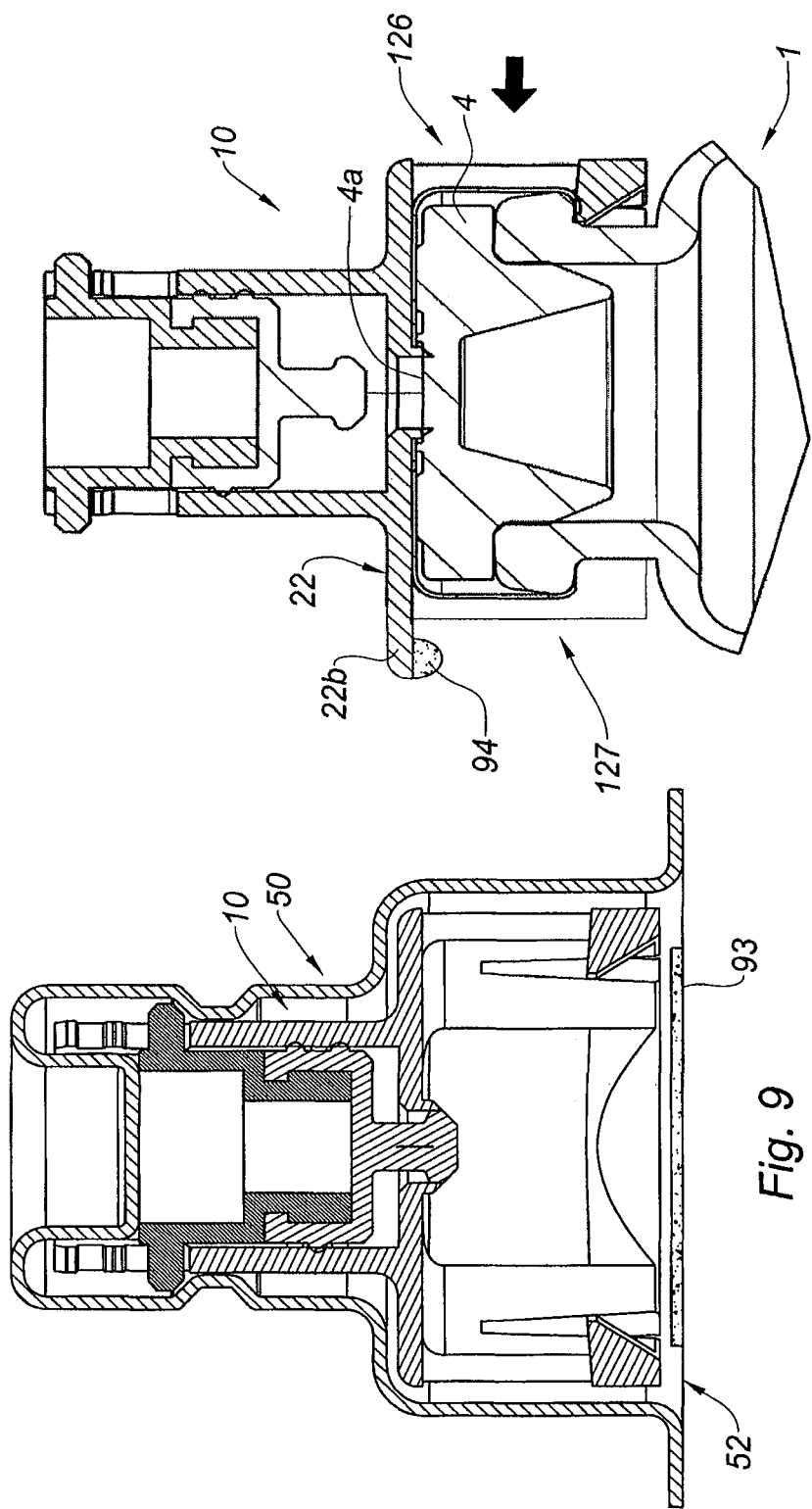

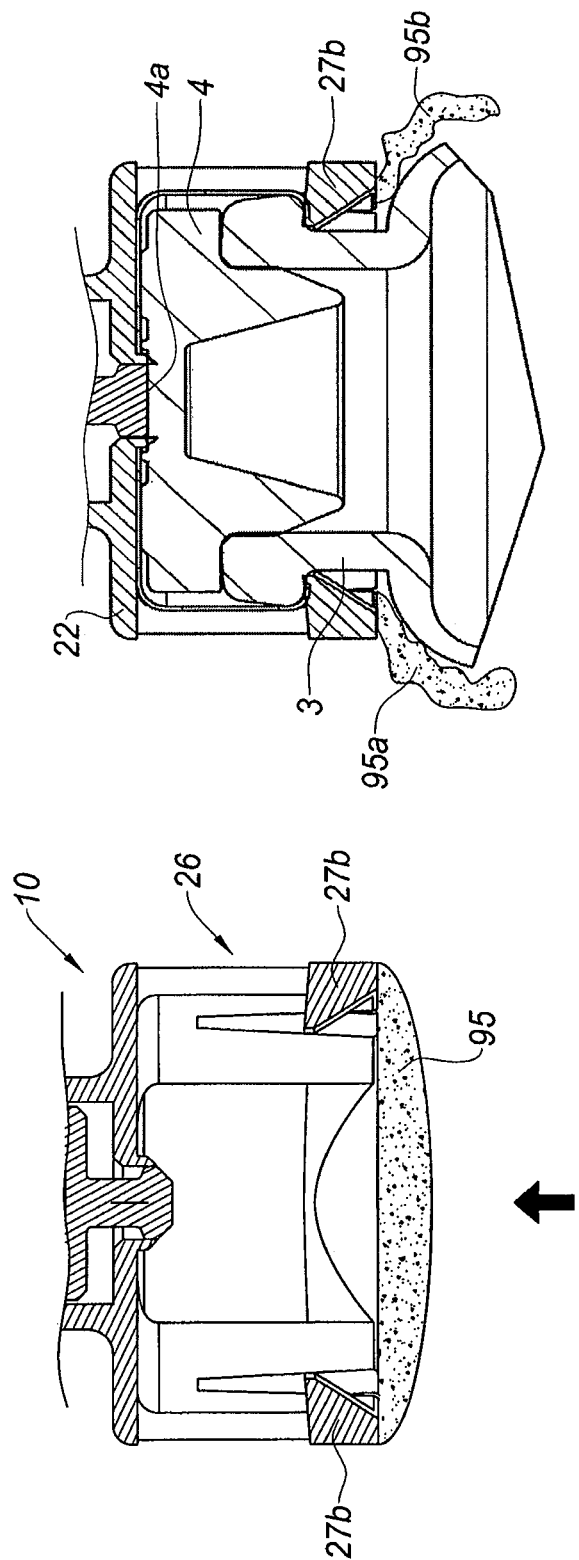

ADAPTOR FOR COUPLING TO A MEDICAL CONTAINER

CROSS-REFERENCE TO RELATED APPLICATIONS

This application is a continuation application of U.S. application Ser. No. 14/375,196 filed Jul. 29, 2014, which is a United States national phase of International Application No. PCT/SG2013/000043 filed Feb. 1, 2013, and claims priority to Singapore Patent Application No. 201200772-0 filed Feb. 2, 2012, the disclosures of each of which are hereby incorporated in their entirety by reference.

BACKGROUND OF THE INVENTION

Field of the Invention

The present invention relates to an adaptor for coupling to a medical container such as a vial containing a pharmaceutical product, such as a vaccine, said adaptor allowing for multiple aseptic needle piercings with an injection device to be filled with part of the product contained in the medical container.

Description of Related Art

In this application, the distal end of a component or apparatus must be understood as meaning the end furthest from the hand of the user and the proximal end must be understood as meaning the end closest to the hand of the user, with reference to the injection device intended to be used with said component or apparatus. As such, in this application, the distal direction must be understood as the direction of injection with reference to the injection device, and the proximal direction is the opposite direction, i.e. the direction of the transfer of the product from the vial to the injection device.

One of the ways to improve health is to immunize entire populations against a number of diseases. To date, injection administration is the most common method of administering vaccines.

Each year, numerous drugs, for example vaccines, need to be prepared throughout the world by healthcare institutions. Many vaccine compositions are usually not stable at room temperatures and they must be stored at rather specific cold temperatures. Indeed, due to their biological nature, vaccines are complex to handle and to store. Vaccines are usually temperature sensitive and typically need to be maintained and stored at all time between 2 and 8 degrees Celsius (° C.). Some vaccines will be more sensitive to heat exposure and others will be sensitive to freezing. Therefore, maintaining and monitoring the appropriate temperatures during the storage and the handling of vaccines is a critical issue in order to sustain their efficacy. Overexposure to heat as well as overcooling may result in the destruction of the biological elements of the vaccines. Use of vaccines not stored in appropriate conditions may lead to not effective vaccination of the populations against diseases and may lead to expensive campaigns with limited results.

Furthermore, it is critical that the cold chain be not interrupted from production of the drug at a pharmaceutical company to its administration to the patient.

From a supply chain perspective, the most efficient vaccine packaging is the multidose container, such as a multidose vial, that is to say, a vial that may contain up to 10, 100 or 1000 doses of vaccine, one dose being intended for one patient. These vials are usually closed by a septum. In preparation of an injection of a vaccine, the user pierces the septum of the medical container with the needle of an empty syringe, he then fills the syringe with one dose of vaccine and proceeds to the injection of the vaccine to the patient.

As such, multidose vials imply that the septum of the vial be pierced successively a high number of times, namely as many as the number of doses present in the vial. In order to ensure safe injections, the sterility of the septum of the vial should be maintained during the whole time the vial is used.

Anyway, in locations where it is difficult to maintain favorable hygienic conditions such as remote locations which are fax from towns and from hospital facilities, the multidose vials may be handled and manipulated at ambiant air. In such cases, the septum of the vial may be contaminated either by the ambiant air, or, each time a dose of vaccine is removed, by the needle of the empty syringe used.

In addition, in regions where there is limited or potentially no supply of energy to power cooling equipment such as a refrigerator, the multidose vials may be maintained in cold conditions by simple contact with ice packs. As time goes by, part of the ice may melt and turn into water, and the septum of the multidose vials may be in contact with such water that may contaminate the septum of the vial.

It may then happen that a multidose medical container, such as for example a 10-dose medical container, is opened and that only three doses are used, for vaccinating three patients only, the remaining content of the medical container being wasted because not intended to be administered in a sufficiently short time after opening of the medical container in order to guaranty the vaccine or drug sterility.

Vaccination campaigns can therefore be made difficult in some regions and a significant proportion of vaccines may be wasted by the time they reach their target. This has an unacceptable cost to the health organizations in charge of immunization campaigns. In addition, it may happen that in case of vaccination campaigns, or pandemic, hundreds of patients need to be vaccinated in a very short time, in locations where it is difficult to maintain favorable hygienic conditions such as locations which are far from towns and from hospital facilities.

Therefore, it would be desirable to provide a device that would allow several successive safe piercings of a multidose vial septum and that would guarranty that said piercing be carried out in aseptic conditions. In particular, it would be desirable to provide a device that would guarranty that the septum be made sterile at the time of injection act, or be maintained sterile during the lifetime of the multidose vial, and that would prevent wastage of the drug, even if the multidose vial is not stored in aseptic conditions.

SUMMARY OF THE INVENTION

A First Aspect of the Present Invention is an Adaptor for Coupling with a Medical Container Having a Collar Closed by a Septum, Said Septum Having an Outer Surface Directed Towards the Outside of the Medical Container, the Adaptor Comprising:

a tubular body substantially closed at its distal end with a transversal wall provided with a central hole and substantially closed at its proximal end by a pierceable elastomeric piece, said pierceable elastomeric piece, transversal wall and tubular body together defining an inner cavity of said adaptor, said pierceable elastomeric piece being movable within said tubular body between a first position, in which a distal part of said pierceable elastomeric piece forms a seal of said central hole, and a second position, proximally spaced from said first position, in which said distal part opens the seal of said central hole, an air inlet for allowing air from the outside to enter said inner cavity at least when said pierceable elastomeric piece moves from its first position to its second position, said air inlet comprising a filtering system for decontaminating said entering air before it reaches said inner cavity, and a gripping member for securing the adaptor to the medical container so that the distal surface of said transversal wall is brought in contact with the outer surface of said septum when said adaptor is secured on said medical container.

The adaptor of the invention is intended to be mounted on a medical container, for example a conventional vial for storing pharmaceutical products, such as multidose vials for vaccines. Such a vial 1 is shown on FIGS. 1A-1C and generally comprises a tubular barrel 2 having a longitudinal axis A, closed at an end and having a collar 3 at the opposite end, said collar 3 being closed by a septum 4. Usually, the septum 4 is fixedly attached to the collar 3 of the vial 1 by a peripheral band 5, said peripheral band 5 leaving a part of the septum 4, herein called outer surface 4a of the septum, directly facing the outside of the vial 1, namely the outside environment. The septum 4 is usually made of a material impermeable to gas and liquid and it seals hermetically the content of the vial 1. The septum 4 is also pierceable by the needle of an injection device intended to be filled with the product contained in the vial, said septum 4 being accessible to said needle via its outer surface 4a.

In the present application, "pierceable" means that the septum or the elastomeric piece of the adaptor may be pierced and traversed by the needle of an injection device such as a syringe, an auto-injector or a reconstitution device, for example for administering a pharmaceutical product such as a drug or vaccine.

The gripping member of the adaptor of the invention may be any member capable of securing the adaptor around the medical container, and in particular around the collar of the medical container, either in a temporary or permanent way.

The adaptor of the invention allows piercing the septum of the medical container in favorable hygienic conditions multiple successive times, and enables the decontamination of outside air likely to enter the medical container. The adaptor is provided to the user with the pierceable elastomeric piece in its first position. Indeed, when the user decides to fill an empty injection device with a dose of drug contained in the medical container, he simply secures the adaptor on the medical container by means of the gripping member, thereby bringing in contact the distal surface of the transversal wall of the adaptor and the outer surface of the septum. After the adaptor has just been secured on the medical container, the pierceable elastomeric piece is still in its first position, and the distal part of the pierceable elastomeric piece sealing the central hole of the transversal wall of the adaptor is in tight contact with the outer surface of the septum of the medical container. The user then causes the pierceable elastomeric piece to transition from its first position to its second position. During this step, the outer surface of the septum replaces the distal part of the pierceable elastomeric piece in its function of sealing the central hole. As a consequence, when the pierceable elastomeric piece moves from its first position to its second position, a vacuum is created in the inner cavity and air from the outside automatically enters via the air inlet. The air inlet is preferably distinct from said central hole. The air from the outside is caused to travel through the filtering system of the air inlet. As a consequence, when the air from the outside reaches the inner cavity, said air is decontaminated. The result is the presence of a cavity filled with decontaminated air, located between the pierceable elastomeric piece of the adaptor and the outer surface of the septum of the medical container. As a consequence, introducing the needle in the medical container implies that the needle pierces and traverses the elastomeric piece of the adaptor in the first place. During this step, the needle mechanically rubs against the material forming the elastomeric piece and it is naturally cleaned, as the potential bacteria are wiped out from the needle when said needle penetrates the elastomeric piece. In addition, once the needle protrudes out of the elastomeric piece of the adaptor, it enters the inner cavity of the adaptor, which is filled with decontaminated air. The needle is therefore not contaminated and it can further enter the septum of the medical container with no risk to be contaminated by any foreign elements.

The user may repeat the piercing step with the needle of a new empty injection device until all the doses contained in the medical container are removed. Indeed, each time a dose of product is removed from the medical container, the vacuum thereby created in the medical container is transferred to the inner cavity via the hole generated in the septum by the needle. The inner cavity consequently sucks additional air from the outside. Since this additional air needs to travel through the filtering system of the air inlet before reaching the inner cavity, this inner cavity remains filled with decontaminated air during the whole process of removing successively several doses of product from the medical container. By preventing all direct contamination via a needle and all indirect contamination from the outside environment, the adaptor of the invention acts as a protection of the septum and of the product stored into the medical container.

In embodiments, the pierceable elastomeric piece is made of a gas and liquid impermeable material capable of flexing under pressure. The pierceable elastomeric piece may show an average thickness ranging from about 0.5 to about 5 mm, preferably from about 1 to about 3 mm. The pierceable elastomeric piece may show a hardness ranging from about 10 to about 100 Shore A, preferably from about 40 to about 70 Shore A, measured according to standard DIN 53505.

Suitable materials for the pierceable elastomeric piece of the adaptor of the invention include natural rubber, acrylate-butadiene rubber, cis-polybutadiene, chloro or bromobutyl rubber, chlorinated polyethylene elastomers, polyalkylene oxide polymers, ethylene vinyl acetate, fluoro silicone rubbers, hexafluoropropylene-vinylidene fluoride-tetrafluoroethyleneterpolymers, butyl rubbers, polyisobutene, synthetic polyisoprene rubber, silicone rubbers, styrene-butadiene rubbers, tetrafluoroethylene propylene copolymers, thermoplastic-copolyesters, thermoplastic elastomers, or the like or a combination thereof.

In embodiments, the pierceable elastomeric piece is self-resealing. By "self-resealing" it is meant that the elastomeric piece closes again the hole produced by the piercing of the needle, automatically and rapidly, for example in less than 0.5 seconds, once the needle is removed from the elastomeric piece. This automatic closure step may occur a high number of times, in particular as many times as necessary for removing the numerous doses of products present in the multidose medical container. Suitable materials for self-resealing pierceable elastomeric piece of the adaptor of the invention include synthetic polyisoprene, natural rubber, silicone rubber, thermoplastic elastomers, or the like or a combination thereof.

In embodiments, the adaptor further comprises a pulling member, safely attached to said pierceable elastomeric piece, for allowing a user to manually move said pierceable elastomeric piece from its first position to its second position. Because the pierceable elastomeric piece substantially closes the proximal end of the tubular body of the adaptor, it is in tight contact against the inner wall of the tubular body and its movement within the tubular body may need significant force. The presence of a pulling member, for example made of a rigid material, safely attached to the pierceable elastomeric piece, and that the user may firmly grasp in his hands, assists the user and makes it easier for him to pull proximally on the pierceable elastomeric piece so as to move it from its first position to its second position.

In embodiments, the adaptor further comprises a locking system for maintaining said pierceable elastomeric piece in its second position. Such a locking system ensures that the pierceable elastomeric piece remains in the adequate position for proceeding safely and in favorable hygienic conditions to the successive removals of doses of product. Moreover, once the adaptor is secured on the medical container, the adaptor constitutes a protection against misuse.

In embodiments, the adaptor comprises a blister surrounding said adaptor in a storage state. In particular, the blister may be made of a rigid shell closed by a pellicle film. Such a blister preserves the sterility of the adaptor prior use and protects it during shipping and storage.

In embodiments, the blister may be removable by proximal force exerted on the blister, and the blister comprises a coupling surface for releasably coupling the blister to the pierceable elastomeric piece during the step of removal of the blister, removal of said blister thereby causing the pierceable elastomeric piece to transition from its first position to its second position. In particular, when the pulling member is present, the blister comprises a coupling surface abutting against a distal face of an outer radial rim of said pulling member when the blister surrounds the adaptor in the storage state of the adaptor. As such, when the user removes the blister by pulling it in the proximal direction, the coupling surface pushes the outer radial rim of the pulling member in the proximal direction. Since the pulling member is safely attached to the pierceable elastomeric piece, this pierceable elastomeric piece is moved in the proximal direction and reaches its second position. The coupling surface of the blister then becomes disengaged from the outer radial rim of the pulling member and the blister is fully removed from the adaptor. The adaptor is therefore easy to use with no other movement required from the user than securing the adaptor on the medical container and removing the blister. Moreover, the blister limits the contamination of the adaptor by the user as no direct contact is required between the adaptor and the user's hands.

In embodiments, the gripping member may be a lateral clipping member capable of being laterally mounted on the collar of said medical container. The lateral clipping member may comprise a U-shaped element intended to be engaged on said collar via the open part of the U-shaped element, the curved part of the U-shaped element partially surrounding the collar, said U-shaped element extending from said transversal wall in the distal direction. For example, the transversal wall may join together the two branches of the U of the U-shaped element.

In other embodiments, the gripping member is an axial clipping member capable of being axially mounted on the collar of said medical container. For example, the axial clipping member may comprise a skirt capable of being axially engaged on said collar, said skirt extending from said transversal wall in the distal direction.

In embodiments, the adaptor further comprises a cleaning pad, said cleaning pad being configured to at least partially slide on said outer surface of said septum when the adaptor is being mounted on the medical container. Such embodiments allow the outer surface of the septum, where the distal tip of the needle is intended to penetrate, to be automatically cleaned before the adaptor is secured to the medical container.

The cleaning pad may be any pad, such as fabric or sponge, for example out of cotton or any other porous material, and may be treated by a cleaning solution. For example, the cleaning pad may comprise a disinfecting agent. In this case, the outer surface of the septum is disinfected before the pierceable elastomeric piece of the adaptor comes in contact with it. The disinfecting agents may be selected from alcohols, such as ethanol or isopropanol, organic solvents, such as nitrofurane, toluene, phenol and derivatives thereof, derivatives of quinoline and acridine, salts such as sodium hypochlorite, sodium chlorite or sodium chlorate, chlorine dioxide, salts of iodine, mercury, silver, ammonium, or the like or a combination thereof. For example, the disinfecting agent may be selected according to the most common bacteria and viruses that may be found in the area of use of the medical container.

In particular, the cleaning pad is provided as a part of the adaptor, for example as a projection extending outwardly from the transversal wall. The user has no additional operation or action to do than simply mounting the adaptor on the medical container. Because of the location and configuration of the cleaning pad on the adaptor, the cleaning pad automatically slides on the outer surface of the septum, thereby wiping out potential bacteria or contamination agents present on said outer surface, when the user completes the step of mounting the adaptor on the collar of the medical container.

For example, in embodiments where the lateral clipping member comprises a U-shaped element intended to be engaged on said collar via the open part of the U, the curved part of the U partially surrounding the collar, the transversal wall may be provided with a projection extending radially in the direction of the free ends of the U, a distal face of said projection being provided with said cleaning pad. As such, when the user approaches the free ends of the U of the lateral clipping member towards the collar of the medical container, the cleaning pad enters in contact with an edge of the outer surface of the septum. While the user continues to move the lateral clipping member towards the collar so as to mount it thereon, the cleaning pad slides on the outer surface of the septum, until it loses contact with said septum when the lateral clipping member reaches its position where it is secured on the collar. In this position, because of its location at the free ends of the U, the cleaning pad does not face the septum anymore and it does not prevent the piercing of the septum by the needle. During the mounting step of the adaptor on the collar as described above, the sliding of the cleaning pad onto the outer surface of the septum wipes out the bacteria and/or contamination elements potentially present on said outer surface. The outer surface of the septum is therefore decontaminated when the elastomeric piece of the adaptor comes in contact with it.

In embodiments where the axial clipping member comprises a skirt capable of being axially engaged on said collar, the cleaning pad may be a breakable membrane attached to the inner wall of the skirt. As such, when the user approaches the distal free end of the skirt towards the collar of the medical container, the breakable membrane enters in contact with the outer surface of the septum. While the user continues to move the axial clipping member distally so as to mount it on the collar of the medical container, the breakable membrane, which is attached to the inner wall of the skirt, becomes stretched out on the outer surface of the septum and finally breaks on said outer surface and is torn in several parts that slide on said outer surface while the axial clipping member reaches its position where it is secured on the collar. In this position, because it is now torn in several parts hanging down from the inner walls of the skirt, the membrane does not face the septum anymore and it does not prevent the piercing of the septum by the needle to take place. During the mounting step of the adaptor on the collar as described above, the sliding of the several torn parts of the breakable membrane on the outer surface of the septum has wiped out the bacteria and/or contamination elements potentially present on said outer surface. The outer surface of the septum is therefore decontaminated when the elastomeric piece of the adaptor comes in contact with it.

In embodiments, the cleaning pad is located on a removable part of said adaptor. For example, said removable part may be removed from said adaptor once said adaptor is secured on said medical container. Such a cleaning pad may be used for additional cleaning by the users of the medical container, the septum and/or other surfaces of the injection device, or even for the cleaning of the patient's skin.

Alternatively, the cleaning pad may be provided on the blister. In embodiments, the removable part on which the cleaning pad is located is a portion of a blister surrounding said adaptor in a storage state. For example, the portion of said blister may remain on the adaptor while the adaptor is mounted on the collar and may be removed thereafter, once the cleaning pad has completed its function of decontaminating the outer surface of the septum.

In embodiments, the adaptor further comprises a pierceable decontamination insert located proximally with respect to said pierceable elastomeric piece. In such embodiments, the distal tip of the needle therefore first pierces the decontamination insert, in which it is decontaminated, then the pierceable elastomeric piece, in which it is submitted to a mechanical cleaning as explained above, before entering in contact with the outer surface of the septum of the vial. For example, the pierceable decontamination insert may be a sterilizing gel.

In embodiments, the inner wall of the inner cavity may be coated with an anti-condensation coating. The temperature changes induced by moving the medical container from a refrigerated storage area to external environment may yield condensation, especially in humid areas. Such condensation, which may lead to an environment suitable for bacteria development on the surface of the inner cavity can thus be avoided. Therefore, the coating acts as a supplemental decontamination system if some contaminants reach the inner cavity.

Another aspect of the invention is an assembly comprising a medical container having a collar closed by a septum, said septum having an outer surface directed towards the outside of the medical container, and an adaptor as described above.

BRIEF DESCRIPTION OF THE DRAWINGS

FIGS. 1A-1C are respectively a perspective view, a partial side view and a partial cross section view of a conventional vial on which the adaptor of the invention is to be mounted, FIG. 2A is a cross section view of an adaptor of the invention in the storage state, FIG. 2B is a cross section view of the adaptor of FIG. 2A just after having been mounted on a vial, FIG. 7 is a cross section view of an alternative embodiment of the adaptor of the invention, FIG. 8 is a cross section view of an alternative embodiment of the adaptor of the invention, FIG. 9 is a cross section view of an alternative embodiment of the adaptor of the invention, FIG. 10 is a cross section view of an alternative embodiment of the adaptor of the invention, FIGS. 12A and 12B are partial cross section views of an alternative embodiment of the adaptor of the invention, provided with a breakable membrane, respectively in the storage position, and once the adaptor has been secured on the vial.

DESCRIPTION OF THE INVENTION

Figures 3A, 3B:
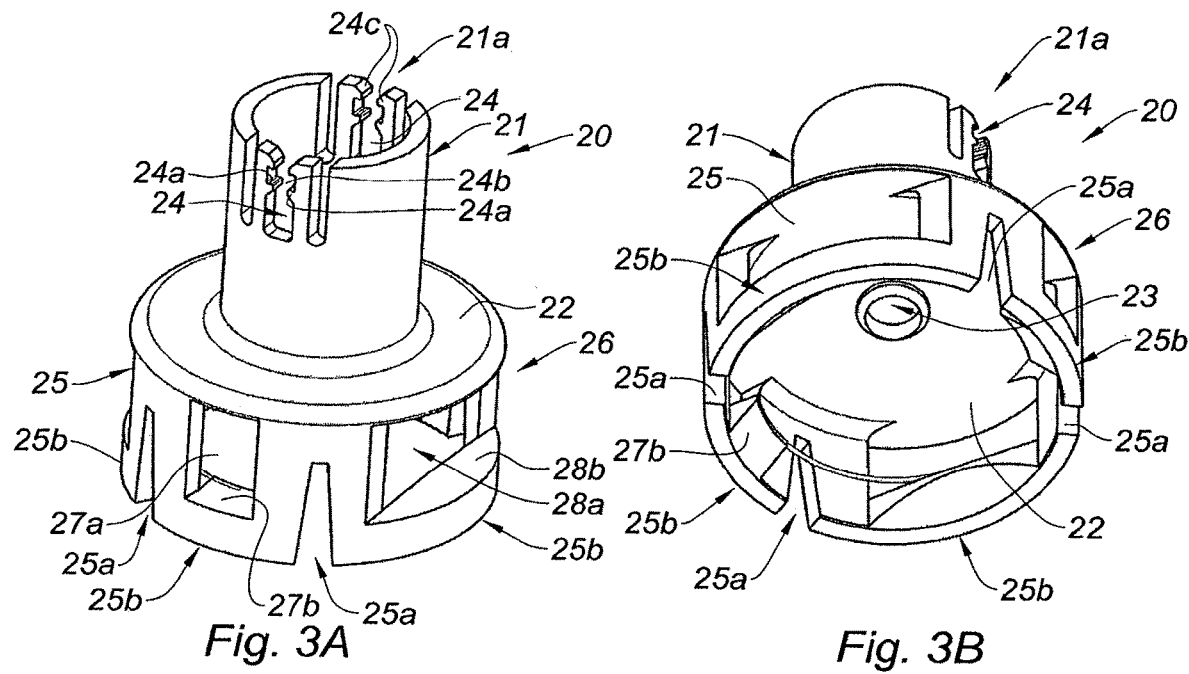
FIGS. 3A-D are respectively a perspective view from the top, a perspective view from the bottom, a side view and a cross section view of the tubular body of the adaptor of FIG. 2A, FIGS. 4A-4C are respectively a perspective view from the top, a perspective view from the bottom, and a side view of the pulling member of the adaptor of FIG. 2A, FIGS. 5A-5C are respectively a perspective view from the top, a perspective view from the bottom, and a cross section view of the pierceable elastomeric piece of the adaptor of FIG. 2A.
Figures 3C, 3D:
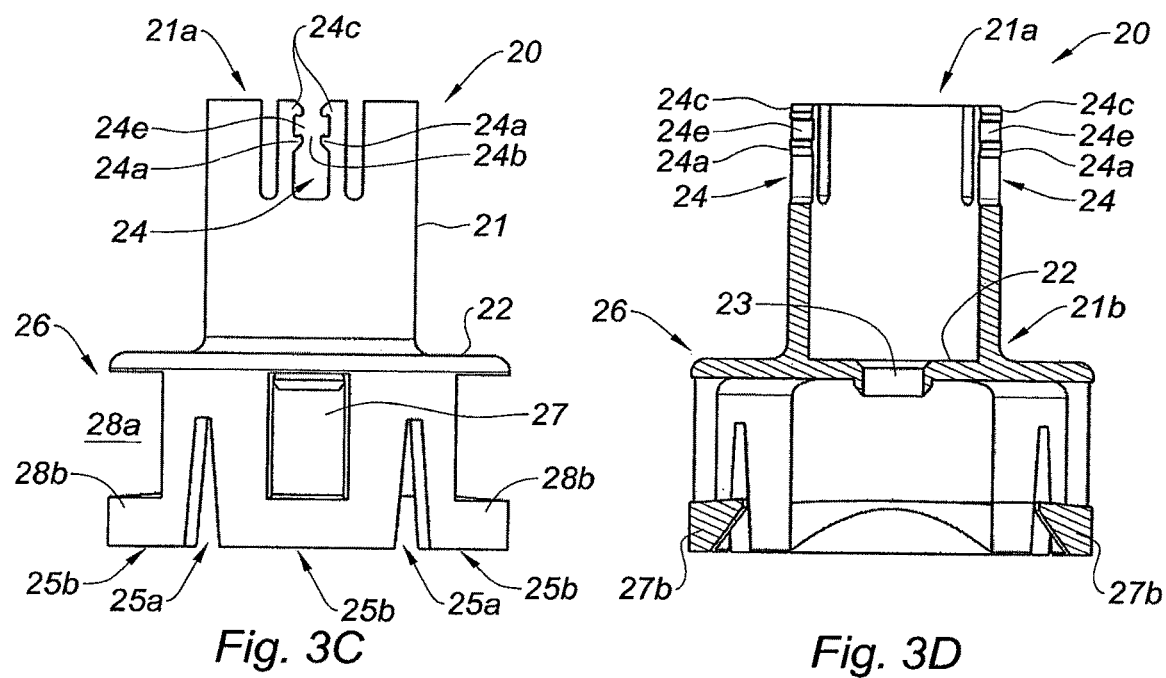

With reference to FIG. 2A is shown an adaptor 10 of the invention, in a storage position. The adaptor 10 is intended to be mounted on a medical container such as the multidose vial 1 as shown on FIGS. 1A-1C.

The adaptor 10 of FIGS. 2A-5C comprises a tubular body 20 receiving a pierceable elastomeric piece 30 and a pulling member 40.

With reference to FIGS. 3A-3D, the tubular body 20 will now be described in detail. The tubular body 20 comprises a tubular element 21 open at its proximal end 21a and substantially closed at its distal end 21b by a transversal wall 22 provided with a central hole 23. The tubular element 21 is provided at its proximal end 21a with two longitudinal windows 24 diametrically opposed. Each window 24 is provided on its lateral walls with two inner pegs 24a facing each other and thereby forming a narrowing 24b of the window 24. Each window 24 is further provided with two proximal pegs 24c facing each other, the inner pegs 24a and the proximal pegs 24c forming altogether a recess 24e.

At the distal end 21b of the tubular element 21, the transversal wall 22 extends radially outwardly beyond the tubular element 21 and is provided with a distal tubular wall 25 so as to form a skirt 26. As will be seen from the description below, the skirt 26 is intended to be used as the gripping member for securing the adaptor 10 on the collar 3 of the vial of FIGS. 1A-C. As such, the skirt 26 is dimensioned and shaped so as to be capable of surrounding the collar 3 of the vial 1 of FIGS. 1A-1C. The distal tubular wall 25 is provided with four distal slots 25a defining four radially outwardly deflecting legs 25b for the distal tubular wall 25. Two oppsite deflecting legs 25b are each provided with a longitudinal window 27a and with an inner radial stop 27b. The two other opposite deflecting legs 25b are each provided with a circumferential window 28a and with an outer radial stop 28b.

With reference to FIGS. 4A-4C, the pulling member 40 will now be described in detail. The pulling member 40 comprises a proximal tubular portion 41 and a distal tubular portion 42, the proximal tubular portion 41 having an outer diameter greater than the outer diameter of the distal tubular portion 42, the proximal and distal tubular portions (41, 42) being linked to each other by an intermediate tubular portion 43 of outer diameter less than the outer diameters of both the proximal and distal tubular portions (41, 42). The intermediate tubular portion 43 therefore forms an annular recess 44 of the pulling member 40.

The outer wall of the proximal tubular portion 41 is provided with two diametrically opposed radial projections 45, the function of which will be explained further below.

As will appear from the description below, the pulling member 40 is dimensioned and shaped so as to be partially received within the pierceable elastomeric piece 30 (FIGS. 5A-5C).

The pulling member 40 is for example made of a rigid material, such as polypropylene, polystyrene, polycarbonate, acrylonitrile butadiene styrene, high-density polyethylene, or the like or a combination thereof.

With reference to FIGS. 5A-5C, the pierceable elastomeric piece 30 will now be described in detail.

The pierceable elastomeric piece 30 comprises a proximal ring 31 defining a central recess 38 closed at its distal end by a transversal wall 32. From the central region of the distal face of the transversal wall 32 extends a cylindrical projection 33 ending with a distal plug 34 having an, outer diameter greater than that of the cylindrical projection 33. The proximal ring 31 is provided at its proximal end with an inner annular rim 35 forming an inner abutment surface 35a in the proximal direction.

The outer surface of the proximal ring 31 is provided with a plurality of interrupted circumferential ridges 36. As will be seen from the description below in connection with FIG. 6B, this plurality of interrupted circumferential ridges 36 define a labyrinthic path 37 for air to circulate from a proximal end 31a to a distal end 31b of the proximal ring 31 when the pierceable elastomeric piece 30 is received within the tubular body 20 of the adaptor 10.

The elastomeric piece 30 is made of a material impermeable to gas and liquid and capable of flexing under pressure. The pierceable elastomeric piece may show an average thickness ranging from about 0.5 to about 5 mm, preferably from about 1 to about 3 mm. The pierceable elastomeric piece may show a hardness ranging from about 10 to about 100 Shore A, preferably from about 40 to about 70 Shore A, measured according to standard DIN 53505.

Suitable materials for the pierceable elastomeric piece of the adaptor of the invention may include natural rubber, acrylate-butadiene rubber, cis-polybutadiene, chloro or bromobutyl rubber, chlorinated polyethylene elastomers, polyalkylene oxide polymers, ethylene vinyl acetate, fluoro silicone rubbers, hexafluoropropylene-vinylidene fluoride-tetrafluoroethyleneterpolymers, butyl rubbers, polyisobutene, synthetic polyisoprene rubber, silicone rubbers, styrene-butadiene rubbers, tetrafluoroethylene propylene copolymers, thermoplastic-copolyesters, thermoplastic elastomers or the like or a combination thereof.

Preferably, the elastomeric piece is self-resealing and it automatically seals the hole produced by the piercing of the needle, automatically and rapidly, for example in less than 0.5 seconds, once the needle is removed from the elastomeric piece. This automatic closure step may occur a high number of times, in particular as many times as necessary for removing the numerous doses of products present in the multidose vial 1. Suitable materials for self-resealing pierceable elastomeric piece of the adaptor of the invention may include synthetic polyisoprene, natural rubber, silicone rubber, thermoplastic elastomers, or the like or a combination thereof.

In embodiments, the pierceable elastomeric piece may further comprise a material including antiseptic agents, such as silver ions or copper ions. For example, silver salt or copper salt may be covalently linked to the polymer matrix of material comprised in the pierceable elastomeric piece. Alternatively, silver salts or copper salts may be included as a load during the manufacturing of the polymer comprised in the pierceable elastomeric piece. For example, the polymer matrix may be selected from silicone rubber, butyl rubber and/or halogenobutyl rubber.

In embodiments, the pierceable elastomeric piece is made of a material comprising a silicone rubber including silver ions: such products are commercially available from the company Momentive Performance Materials under the tradename "Statsil®" or "Addisil®". In other embodiments, the pierceable elastomeric piece consists in a material including silver ions, such as silicone rubber including silver ions. In other embodiments, the pierceable elastomeric piece may consist in a material including copper ions.

Pierceable elastomeric pieces of the adaptor of the invention, comprising a material including antiseptic agents, such as silver ions or copper ions, show antiseptic properties. The growth of bacteria at the surface of the pierceable elastomeric piece is therefore directly prevented. These materials also show hydrophobic properties which prevent condensation formation, thereby further reducing growth of bacteria. As a consequence, when a needle pierces a pierceable elastomeric piece including such antiseptic agents, in view of entering a vial for removing a dose of product from said vial, the risk of contamination of the vial content is reduced.

Alternatively or in combination, the pierceable elastomeric piece may comprise a coating comprising an antiseptic agent, such as chlorhexidine di-acetate. For example, the pierceable elastomeric piece may comprise a butyl rubber or a halogenobutyl rubber coated with a coating comprising chlorhexidine di-acetate. Such a coating may be obtained by UV cross-linking. The antiseptic action of such a coating may occur within minutes and such a coating may therefore be able to clean a contaminated needle during its insertion within the pierceable elastomeric piece.

The use of adaptor 10 of FIG. 2A with a vial of FIGS. 1A-C will now be explained with reference to FIGS. 1A-6B.

With reference to FIG. 2A, the adaptor 10 is in a storage position and it is packaged in a blister 50 surrounding it completely. In the example shown, the blister 50 comprises a rigid shell 51 surrounding the adaptor except for the distal open end of the skirt 26, which is closed by a tearable pellicle film 52.

In this storage position, the pierceable elastomeric piece 30 is received within the tubular element 21, the outer surface of the proximal ring 31 being in tight contact with the inner wall of the tubular element 21. The proximal ring 31 therefore substantially closes the proximal end 21a of the tubular element 21. Nevertheless, because of the presence on the outer surface of the proximal ring 31 of the plurality of interrupted circumferential ridges 36 defining a labyrinthic path 37 as explained above, air from the ouside will be able to circulate from a proximal end 31a of the proximal ring 31 to its distal end 31b, once the blister 50 or the pellicle film 52 is removed, as will be described below. In this position also, the pierceable elastomeric piece is in a first position, in which the distal plug 34 of the pierceable elastomeric piece 30 seals the central hole 23 of the transversal wall 22.

The pierceable elastomeric piece 30, the transversal wall 22 and the inner wall of the tubular body 20 therefore define together an inner cavity 60 of the adaptor 10. As seen above, the labyrinthic path 37 present on the outer surface of the proximal ring 31 of the pierceable elastomeric piece 30 ends at the distal end 31b of the proximal ring 31 which is directly connected to the inner cavity 60.

As shown in FIG. 2A, the pulling member 40 is safely attached to the pierceable elastomeric piece 30. Indeed, the distal tubular portion 42 is received in the central recess 38 of the proximal ring 31 and the inner annular rim 35 is engaged in the annular recess 44 of the pulling member 40.

In this storage position and first position of the pierceable elastomeric piece 30, the radial projections 45 of the pulling member are engaged in the distal region of the windows 24 of the tubular element 21, as shown on FIG. 2A.

In addition, as shown in FIG. 2A, the outer surface of proximal tubular portion 41 of the pulling member 40 is not in tight contact with the inner wall of the tubular element 21. As a consequence, a tubular space 70 is present between the outer surface of proximal tubular portion 41 of the pulling member 40 and the inner wall of the tubular element 21. This tubular space 70 is in connection, at its distal end with the labyrinthic path 37 present on the outer surface of the proximal ring 31 and which ends directly in the inner cavity 60, and, at its proximal end with the window 24, and consequently with the outside air once the blister 50 and pellicle film 52 are removed from the adaptor. The window 24, the tubular space 70 and the labyrinthic path 37 form altogether an air inlet 80 for entry of air from the outside, once the blister 50 and pellicle film 52 are removed, towards the inner cavity 60.

Once the user is ready to proceed to the withdrawal of a dose of product contained in the vial 1, he removes the pellicle film 52 in order to open the blister 50. In the embodiment shown on FIG. 2B, the shell 51 remains on the adaptor 10 until the adaptor 10 is secured on the collar 3 of the vial 1, and it is removed thereafter. In other embodiments, the whole blister 50 may be removed before mounting the adaptor 10 on the vial 1.

With the shell 51 still present around the adaptor 10, the user moves the distal free end of the skirt 26 of the tubular body 20 towards the collar 3 of the vial 1, and he mounts the adaptor 10 on the collar 3 by axial clipping of the skirt 26 on the collar 3 of the vial 1, as shown in FIG. 2B. As shown in this Figure, the distal surface of the transversal wall 22 is now in contact with the outer surface 4a of the septum 4. In particular, the distal plug 34 of the pierceable elastomeric piece 30 is pressed against the outer surface 4a of the septum 4 of the vial 1. In addition, because of the pegs 27b are engaged in the collar 3 of the vial 1, the adaptor 10 is firmly secured onto the collar 3, and in particular, the septum 4 is firmly pressed against the transversal wall 22.

In the next step, the user removes the shell 51 by pulling it in the proximal direction as indicated by the arrow on FIG. 2B. The rigid shell 51 comprises sloped surfaces 53 which are in abutment against the radial projections 45. When the user pulls on the rigid shell 51 in the proximal direction, the sloped surfaces become coupled to the radial projections 45. As a consequence, since the pulling member 40 is safely attached to the pierceable elastomeric piece 30, the elastomeric piece 30 becomes coupled to the sloped surfaces 53 via the radial projections of the pulling member 40, and both the pulling member 40 and the pierceable elastomeric piece 30 are drawn in the proximal direction (not shown). Once each radial projection 45 reaches the recess 24e of window 24, it becomes engaged therein, and the proximal movement of the pulling member 40 and pierceable elastomeric piece 30 is stopped, while the sloped surfaces 53 are disengaged from the radial projections 45 as the user continues fully removing the rigid shell 51.

Figure 6B:
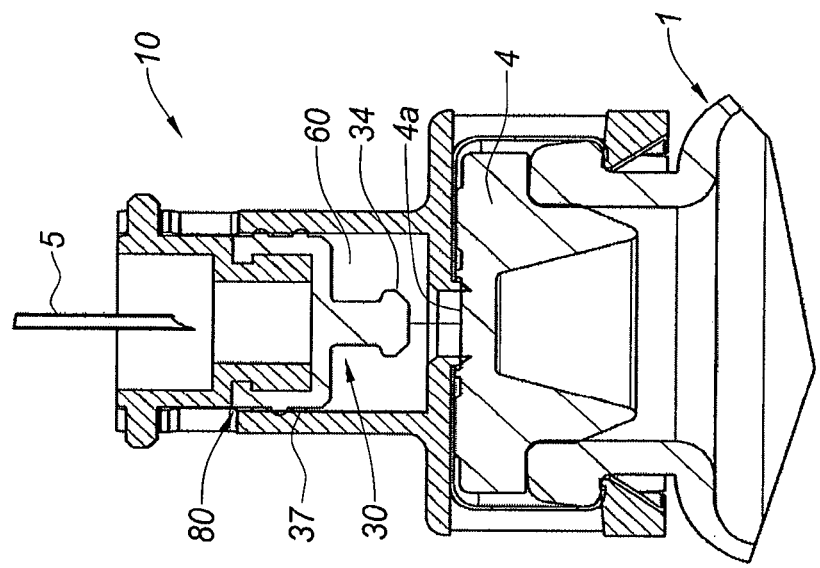
FIG. 6B is a partial view of FIG. 6A at a larger scale.
Figure 6A:
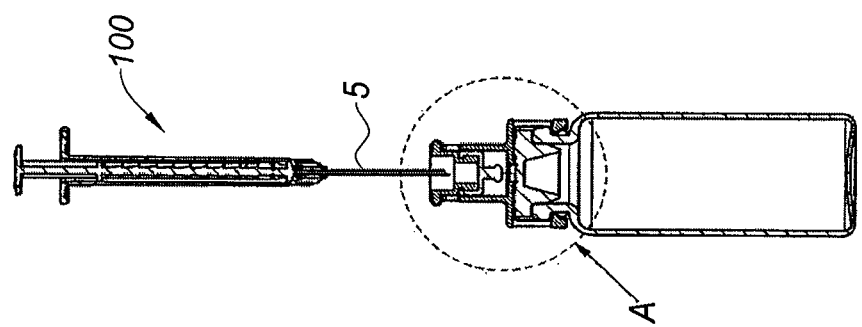
FIG. 6A is a cross section view of the adaptor of FIG. 2A once secured on the vial, with the pierceable elastomeric piece in its second position, and ready to be used in connection with an injection device.

The pierceable elastomeric piece 30 thus reaches its second position, as shown in FIGS. 6A-B, proximally spaced from its first position with respect to the tubular body 20, in which the distal plug 34 releases the seal of the central hole 23.

Because of the outer surface 4a of the septum 4 being in tight contact with the distal surface of the transversal wall 22, while the user causes the pierceable elastomeric piece to transition from its first position to its second position, the outer surface 4a of the septum 4 replaces the distal plug 34 of the pierceable elastomeric piece 30 in its function of sealing the central hole 23 of the transversal wall 22: as a consequence, when the pierceable elastomeric piece 30 is moved from its first position to its second position, a vacuum is created in the inner cavity 60 and air from the outside automatically enters the inner cavity 60 via the air inlet 80 formed by the combination of the window 24, the tubular space 70 and the labyrinthic path 37. The air from the outside is caused to travel through the labyrinthic path 70, said labyrinthic path 70 forming a filtering system for decontaminating air: as a consequence, when the air from the outside reaches the inner cavity 60, said air is decontaminated.

Therefore, in the second position of the pierceable elastomeric piece 30 as shown on FIGS. 6A-B, the inner cavity 60 is filled with decontaminated air. Since this inner cavity 60 is located between the pierceable elastomeric piece 30 of the adaptor 10 and the outer surface 4a of the septum 4 of the vial 1, introducing the needle 5 of an injection device 100 to be filled with a dose of the product contained in the vial 1 in the vial as shown in FIGS. 6A-B demonstrates that the needle 5 pierces and traverses the elastomeric piece 30 of the adaptor 10 in the first place. During this step, the needle 5 mechanically rubs against the material forming the elastomeric piece 30 and it is naturally cleaned, as the potential bacteria are wiped out from the needle 5 when said needle 5 penetrates the elastomeric piece 30. In addition, once the needle 5 protrudes out of the elastomeric piece 30 of the adaptor 10 via the distal plug 34, it enters the inner cavity 60, which is filled with decontaminated air. The needle 5 is therefore not contaminated and it can further enter the septum 4 of the vial 1 with no risk to be contaminated by any foreign elements.

The user may repeat the piercing step with the needle 5 of a new empty injection device 100 until all the doses contained in the vial 1 are removed. Indeed, each time a dose of product is removed from the vial 1, the vacuum thereby created in the vial 1 is transferred to the inner cavity 60 via the hole generated in the septum 4 by the needle 5. The inner cavity 60 consequently draws additional air from the outside. Since this additional air needs to go through the filtering system formed by the labyrinthic path 37 of the air inlet 80 before reaching the inner cavity 60, the inner cavity 60 remains filled with decontaminated air during the whole process of removing successively several doses of product from the vial 1. By avoiding all direct contamination via a needle and all indirect contamination from the outside air, the adaptor 10 of the invention acts as a protection of the septum 4 during the lifetime of the vial 1.

During the whole process of removing one or more doses of product from the vial 1, the pierceable elastomeric piece 30 is maintained in its second position by means of radial projections 45 being engaged in the recess 24e of window 24. The radial projections 45 and the recess 24e therefore form a locking system for maintaining the pierceable elastomeric piece 30 in its second position. Due to this locking system the adaptor 10, once secured on the collar 3 of the vial 1, constitutes a protection against misuse of the product stored in the vial 1. A secured adaptor can thus serve as a proof of sterility of the drug or vaccine stored inside the vial 1.

FIGS. 7-12B show other embodiments of the adaptor 10 of FIGS. 2A-6B. The references designating the same elements as in FIGS. 2A-6B have been maintained on FIGS. 7-12B.

With reference to FIG. 7 is shown the adaptor 10 of FIGS. 2A-6B for which the inner wall of the inner cavity 60 is provided with a anti-condensation coating 90. When a medical container, such as a vial 1, is moved from a refrigerated storage area to an external environment, the difference of temperature may yield condensation, particularly in humid areas. The condensation is a favorable environment for bacteria development and it may form on the surface of the inner cavity 60. Using an anti-condensation coating allows avoiding contamination, even in the case where a bacteria reaches the inner cavity. As a result, neither the needle 5 of the injection device nor the product stored in the vial 1 are contaminated.

With reference to FIG. 8 is shown the adaptor 10 of FIGS. 2A-6B further comprising a pierceable decontamination insert 91 located proximally with respect to the pierceable elastomeric piece 30. On the embodiment shown, the decontamination insert 91 comprises a sterilizing gel 92. For proceeding to the withdrawal of a dose of product from the vial 1, the needle 5 first goes through the sterilizing gel 92, in which it is sterilized, then through the elastomeric piece 30, in which it is submitted to a mechanical cleaning, then in the inner cavity 60 filled with decontaminated air before it contacts the septum 4. The piercing is therefore completed in improved hygienic conditions, as only decontaminated air may be introduced inside the vial 1.

FIGS. 9-12B show embodiments of the adaptor 10 of the invention further comprising a cleaning pad.

The cleaning pad may be any pad, such as fabric or sponge, for example out of cotton or any other porous material, and may be imbibed with a cleaning solution or disinfecting composition. For example, the cleaning pad 60 may comprise a disinfecting agent. The disinfecting agents may be selected from alcohols, such as ethanol or isopropanol, organic solvents, such as nitrofurane, toluene, phenol and derivatives thereof, derivatives of quinoline and acridine, salts such as sodium hypochlorite, sodium chlorite or sodium chlorate, chlorine dioxide, salts of iodine, mercury, silver, ammonium, or the like or a combination thereof. For example, the disinfecting agent may be selected according to the most common bacteria and viruses that may be found in the area of use of the vial.

In the embodiment as shown on FIG. 9, the cleaning pad 93 is provided in the blister 50, for example lying on the inner surface of the pellicle film 52, and the user may use the cleaning pad 93 after having removed the pellicle film 52, for cleaning manually the outer surface 4a of the septum 4 before mounting the adaptor 10 and shell 51 on the vial 1.

Figure 11:
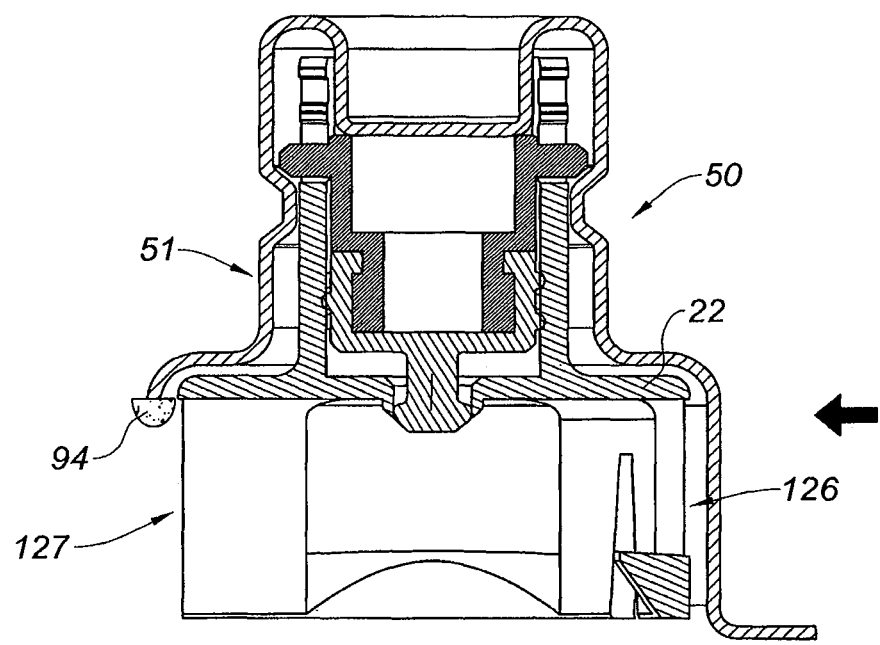
FIG. 11 is a cross section view of an alternative embodiment of the adaptor of the invention.

In embodiments, such as shown on FIGS. 10-11, the cleaning pad is configured so as to at least partially slide on the outer surface 4a of the septum 4 during the step in which the adaptor 10 is being mounted on the vial 1 to be secured thereon.

With reference to FIG. 11, the gripping member is a lateral clipping member capable of being laterally mounted on the collar 3 of the vial 1 under the form of a U-shaped element 126 intended to be engaged on the collar 3 via the open part 127 of the U, along the direction indicated by the arrow of FIG. 11, the curved part of the U partially surrounding the collar 3, the U-shaped element 126 extending from the transversal wall 22 in the distal direction. The blister 50 is adapted to the shape of the U-shaped element 126 and the pellicle film (already removed on FIG. 11) also faces the open part 127 of the U-shaped element 126. As appears from FIG. 11, a cleaning pad 94 is provided on the rigid shell 51, facing the open part 127 of the U-shaped element 126.

Once the user has removed the pellicle film in order to open the blister 50, he approaches the adaptor 10 with the shell 50 towards the collar 3 of vial 1 (not shown), in order to mount laterally the adaptor 10 onto the collar 3 of the vial 1. The cleaning pad 94 enters first in contact with an edge of the outer surface 4a of the septum 4. While the user continues to move laterally the adaptor 10, and thus the U-shaped element 126 towards the collar 3 so as to mount it thereon, the cleaning pad 94 slides on the outer surface 4a of the septum 4, until it loses contact with said septum 4 when the U-shaped element 126 reaches its position where it is secured on the collar 3.

During the mounting step of the adaptor 10 on the collar 3 as described above, the sliding of the cleaning pad 94 onto the outer surface 4a of the septum 4 has wiped out the bacteria and/or contamination elements potentially present on said outer surface 4a. The outer surface 4a of the septum 4 is therefore decontaminated when the elastomeric piece 30 of the adaptor 10 comes in contact with it.

In another embodiment shown on FIG. 10, the blister 50 is fully removed before mounting the adaptor 10 on the vial 1, and the cleaning pad 94 is provided on distal face of a projection 22b of the transversal wall 22, said projection 22b extending radially in the direction of the free ends of the U of the U-shaped element 126. The cleaning step of the outer surface 4a of the septum 4 of embodiment of FIG. 10 is completed in the same way as described for embodiment of FIG. 11.

With reference to FIGS. 12A and 12B is shown schematically another embodiment of the adaptor 10 of the invention of FIGS. 2A-6B, with the skirt 26 as axial clipping member of the adaptor 10. In this embodiment, as shown on FIG. 12A, the cleaning pad is a breakable membrane 95 attached to the inner wall of the distal end of the skirt 26.

As such, when the user approaches the distal free end of the skirt 26 towards the collar 3 of the vial 1, the breakable membrane 95 enters in contact with the outer surface 4a of the septum 4. While the user continues to move the skirt 26 distally so as to mount the adaptor 10 on the collar 3 of the vial 1, the breakable membrane 95, which is attached to the inner wall of the skirt 26, becomes stretched out on the outer surface 4a of the septum 4 and finally breaks on said outer surface 4a. The membrane 95 is torn in several parts (95a, 95b) that slide on the outer surface 4a while the skirt 26 reaches its position where it is secured on the collar 3. In this position, as shown on FIG. 12B, because it is now torn in several parts (95a, 95b) hanging down from the inner walls of the skirt 26, the membrane 95 does not face the septum 4 anymore and it does not prevent the piercing of the septum 4 by the needle of an injection device (not shown). During the mounting step of the adaptor 10 on the collar 3 as described above, the sliding of the several torn parts (95a, 95b) of the breakable membrane 95 on the outer surface 4a of the septum 4 has wiped out the bacteria and/or contamination elements potentially present on said outer surface 4a. The outer surface 4a of the septum 4 is therefore decontaminated when the distal plug 34 of the elastomeric piece 30 of the adaptor 10 comes in contact with it, as shown on FIG. 12B.

Additionally, in all the previous described embodiments of the present invention, the adaptor 10 can be provided with a time monitoring system (not shown). Indeed, and according to current health policies, the content of the vial 1 is usually considered as unsafe for injection after a limited period of time, for example until 28 to 30 days, even if an adaptor 10 according to the present invention is mounted of the vial 1. Therefore, a time monitoring system can be added to the adaptor according to the invention in order to monitor the elapsing time from the first dose withdrawing or to indicate to the user what is the time remaining before the 28 or 30 days deadline.

This time monitoring system could be an electronic timer or a system based on the diffusion of ink into a circuit. For example, the elapsing or remaining time can be monitored by the kinetic of ink progression in a microfluidic circuit. Such systems are particularly attractive because they are small and reliable. For example, such a system could be integrated onto the outside surface of the tubular body 20, for example on the tubular element 21 or on the transversal wall 22. Such systems are commercially available under the trademark Timestrip®.

Furthermore, the time monitoring system could be triggered either manually by the user or automatically. An automatic trigger could occur when the adaptor 10 is mounted on the collar 3 of the vial 1, which assumes a first dose withdrawing shortly afterwards. For example, such time monitoring label, placed on an adaptor 10 could be triggered by an additional peg (not shown) placed into the blister 50 that comes in contact with the time monitoring system and therefore activates it when the user applies a distal pressure on the top of the shell 51.

Such a time monitoring system is valuable to prevent the injection of potentially expired vaccines or drugs to patients. Moreover, it also facilitates the supply chain or stock management in drugstores and avoids wastage of valuable drugs and vaccines by encouraging the use of the first opened vials.

The adaptor of the invention allows for the repeated withdrawal of doses of product contained in a multidose vial in favorable hygienic conditions.

What is claimed is:

1. A package for an aseptic application of an adaptor to a collar of a medical container, the adaptor comprising a tubular body and a pierceable elastomeric piece positioned within the tubular body, the tubular body having a distal end including a transversal wall, the transversal wall including a central hole and a skirt extending in a distal direction therefrom creating a distal open end, the package comprising:
    a blister pack for surrounding the adaptor, the blister pack comprising a shell substantially surrounding the adaptor except for the distal open end of the skirt; and
    a film covering the distal open end of the skirt, wherein upon removal of the film, the distal open end of the skirt is secured to the collar with the shell remaining in place until the pierceable elastomeric piece is moved within the tubular body between a first positon, in which a distal part of the pierceable elastomeric piece forms a seal with the central hole, and a second position, in which the distal part is displaced from the central hole.

2. The package of claim 1, wherein the shell comprises a coupling surface for releasably coupling the shell to the pierceable elastomeric piece during application of a proximal force to the shell during removal thereof, and wherein removal of said shell causes the pierceable elastomeric piece to transition from the first position to the second position.

3. The package of claim 2, wherein continued application of the proximal force to the shell causes the elastomeric piece to lock into a window located at a proximal end of the tubular body.

4. The package of claim 1, including a cleaning pad located within the blister pack.

5. The package of claim 4, wherein the cleaning pad is located adjacent the film.

6. A method for an aseptic coupling of an adaptor to a collar of a medical container, the adaptor comprising a tubular body and a pierceable elastomeric piece positioned within the tubular body, the tubular body having a distal end including a transversal wall, the transversal wall including a central hole and a skirt extending in a distal direction therefrom creating a distal open end, the method comprising:
    enclosing the adaptor in a blister pack, the blister pack comprising a shell substantially surrounding the adaptor except for the distal open end of the skirt and a film covering the distal open end of the skirt;
    removing the film to expose the distal open end of the skirt; and
    securing the distal open end of the skirt to the collar with the shell remaining in place until the pierceable elastomeric piece is moved within the tubular body between a first position, in which a distal part of the pierceable elastomeric piece forms a seal with the central hole, and a second position, in which the distal part is displaced from the central hole.

7. The method of claim 6, wherein the shell comprises a coupling surface and wherein the application of a proximal force to the shell releasably couples the shell to the pierceable elastomeric piece, and wherein removal of said shell causes the pierceable elastomeric piece to transition from the first position to the second position.

8. The method of claim 7, wherein continued application of the proximal force to the shell causes the elastomeric piece to lock into a window located at a proximal end of the tubular body.

9. The method of claim 6, including providing a cleaning pad within the blister pack at an accessible location upon removal of the film.

10. The method of claim 9, including using the cleaning pad to manually clean an outer portion of the medical container prior to securing the adaptor thereto.

* * * * *